United States Patent [19]
Weadock et al.

[11] Patent Number: 6,162,247
[45] Date of Patent: Dec. 19, 2000

[54] VASCULAR GRAFT IMPREGNATED WITH A HEPARIN-CONTAINING COLLAGEN SEALANT

[75] Inventors: Kevin Weadock, Somerset; David J. Lentz, Randolph; Jack Tant, Wayne, all of N.J.

[73] Assignee: Meadox Medicals, Inc., Oakland, N.J.

[21] Appl. No.: 09/217,644

[22] Filed: Dec. 21, 1998

Related U.S. Application Data

[63] Continuation of application No. 08/733,544, Oct. 18, 1996, Pat. No. 5,851,230, which is a continuation of application No. 08/289,792, Aug. 12, 1994, abandoned.

[51] Int. Cl.$^7$ .............................. A61F 2/06; A61L 27/24; A61L 33/10
[52] U.S. Cl. .................. 623/1.47; 623/1.43; 623/921; 530/356; 424/422; 424/423
[58] Field of Search .................................. 623/1, 12, 66, 623/901, 1.47, 1.53, 1.43, 1.5, 921; 424/422, 423; 530/356

[56] References Cited

U.S. PATENT DOCUMENTS

| | | |
|---|---|---|
| 3,106,483 | 10/1963 | Kline . |
| 3,272,204 | 9/1966 | Artandi et al. . |
| 3,425,418 | 2/1969 | Chvapil et al. . |
| 3,479,670 | 11/1969 | Medell . |
| 3,688,317 | 9/1972 | Kurtz . |

(List continued on next page.)

FOREIGN PATENT DOCUMENTS

| | | |
|---|---|---|
| 000 949 A1 | 8/1978 | European Pat. Off. . |
| 241 838 A1 | 10/1987 | European Pat. Off. . |
| 246 638 A2 | 11/1987 | European Pat. Off. . |
| 1601323 | 8/1970 | France . |
| 2029155 | 10/1970 | France . |

(List continued on next page.)

OTHER PUBLICATIONS

R. Guidoin, et al., "Expanded Polytetrafluoro–ethylene Arterial Prostheses in Humans: Histopathological Study of 298 Surgically Excised Grafts," *Biomaterials*, 14, p. 678–693 (1993).

M. Kadletz, et al., "In Vitro Lining of Fibronectin Coated PTFE Grafts with Cryopreserved Saphenous Vein Endothelial Cells," *Thorac. Cardiovasc. Surgeon*, 35, p. 143–147 (1987).

J. Kaehler, et al, "Precoating Substrate and Surface Configuration Determine Adherence and Spreading of Seeded Endothelial Cells on Polytetrafluoroethylene Grafts," *Journal of Vascular Surgery*, 9, p. 535–541 (1989).

P. B. Mansfield, et al., "Preventing Thrombus on Artificial Vascular Surfaces: True Endothelial Cell Linings," *Trans. Amer. Artif. Int. Organs*, 21, p. 264–272 (1975).

L. R. Sauvage, et al., "Dacron® Arterial Grafts: Comparative Structures and Basis for Successful Use of Current Prostheses," *Vascular Graft Update: Safety and Performance, ASTM STP898*, p. 16–24 (1986).

L. R. Sauvage, et al, "Experimental Coronary Artery Surgery: Preliminary Observations of Bypass Venous Grafts, Longitudinal Arteriotomies, and End–to–End Anastomoses," *Journal of Thoracic and Cardiovascular Surgery*, 46, p. 826–836 (1963).

L. R. Sauvage, "Graft Complications in Relation to Prosthesis Healing," *Aortic and Peripheral Arterial Surgery*, p. 427–440.

L. R. Sauvage, et al, *Grafts for the 80's*, p. 1–44 (1980).

*Primary Examiner*—David H. Willse
*Assistant Examiner*—Choon P. Koh
*Attorney, Agent, or Firm*—Hoffmann & Baron, LLP

[57] ABSTRACT

A heparin-collagen dispersion is provided for impregnating a vascular prosthesis with heparin and collagen. The dispersion is prepared at an alkaline pH to allow the addition of heparin without causing the agglutination of collagen from the dispersion. The impregnation of collagen and heparin within the prosthesis effectively prevents blood loss and thrombus formation after implantation of the prosthesis.

14 Claims, 1 Drawing Sheet

U.S. PATENT DOCUMENTS

| | | |
|---|---|---|
| 3,805,301 | 4/1974 | Liebig . |
| 3,808,113 | 4/1974 | Okamura et al. . |
| 3,928,653 | 12/1975 | Dowell, Jr. et al. . |
| 3,953,566 | 4/1976 | Gore . |
| 4,047,252 | 9/1977 | Liebig et al. . |
| 4,113,912 | 9/1978 | Okita . |
| 4,164,254 | 8/1979 | Ward et al. . |
| 4,167,045 | 9/1979 | Sawyer . |
| 4,193,138 | 3/1980 | Okita . |
| 4,219,520 | 8/1980 | Kline . |
| 4,229,838 | 10/1980 | Mano . |
| 4,254,180 | 3/1981 | Kline . |
| 4,280,954 | 7/1981 | Yannas et al. . |
| 4,332,035 | 6/1982 | Mano . |
| 4,349,467 | 9/1982 | Williams et al. . |
| 4,355,426 | 10/1982 | MacGregor . |
| 4,416,028 | 11/1983 | Eriksson et al. . |
| 4,713,070 | 12/1987 | Mano . |
| 4,747,848 | 5/1988 | Maini . |
| 4,784,659 | 11/1988 | Fleckenstein et al. . |
| 4,804,381 | 2/1989 | Turnia et al. . |
| 4,814,120 | 3/1989 | Huc et al. . |
| 4,822,361 | 4/1989 | Okita et al. . |
| 4,833,200 | 5/1989 | Noishiki et al. . |
| 4,837,024 | 6/1989 | Michaeli . |
| 4,841,962 | 6/1989 | Berg et al. . |
| 4,842,275 | 6/1989 | Hoffman, Jr. et al. . |
| 4,902,290 | 2/1990 | Fleckenstein et al. . |
| 4,911,713 | 3/1990 | Sauvage et al. . |
| 4,921,495 | 5/1990 | Kira . |
| 4,973,609 | 11/1990 | Browne . |
| 5,024,671 | 6/1991 | Tu et al. . |
| 5,034,265 | 7/1991 | Hoffman et al. . |
| 5,037,377 | 8/1991 | Alonso . |
| 5,061,276 | 10/1991 | Tu et al. . |
| 5,061,281 | 10/1991 | Mares et al. . |
| 5,108,424 | 4/1992 | Hoffman, Jr. et al. . |
| 5,110,527 | 5/1992 | Harada et al. . |
| 5,118,524 | 6/1992 | Thompson et al. . |
| 5,120,833 | 6/1992 | Kaplan . |
| 5,131,907 | 7/1992 | Williams et al. . |
| 5,141,522 | 8/1992 | Landi et al. . |
| 5,178,630 | 1/1993 | Schmitt . |
| 5,192,310 | 3/1993 | Herweck et al. . |
| 5,197,977 | 3/1993 | Hoffman, Jr. et al. . |
| 5,851,230 | 12/1998 | Weadock et al. . |

FOREIGN PATENT DOCUMENTS

| | | |
|---|---|---|
| 2 318 189 | 2/1977 | France . |
| 1491218 | 4/1969 | Germany . |
| 1494939 | 6/1969 | Germany . |
| 21 19 004 | 6/1969 | Germany . |
| 26 01 289 | 7/1977 | Germany . |
| 28 43 963 | 4/1980 | Germany . |
| (11) 904693 | 2/1982 | U.S.S.R. . |
| 2 092 944 | 8/1982 | United Kingdom . |
| PCT/US83/00574 | 10/1983 | WIPO . |
| WO 83/03536 | 10/1983 | WIPO . |
| WO 92/03764 | 11/1992 | WIPO . |

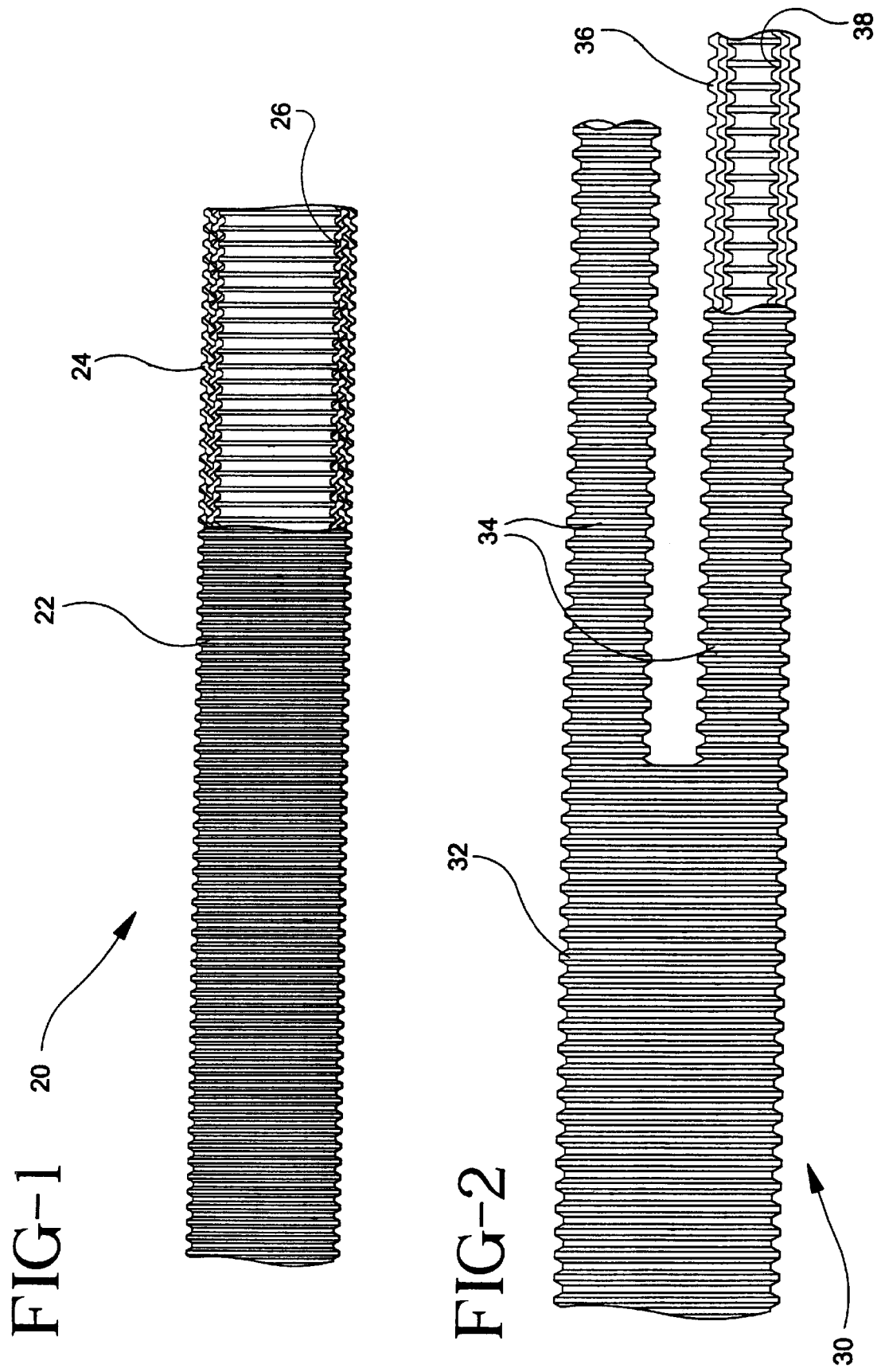

VASCULAR GRAFT IMPREGNATED WITH A HEPARIN-CONTAINING COLLAGEN SEALANT

This application is a continuation of Ser. No. 08/733,544, filed Oct. 18, 1996, U.S. Pat. No. 5,851,230, which is a continuation of Ser. No. 08/289,792 filed Aug. 12, 1994, abandoned.

BACKGROUND OF THE INVENTION

The present invention relates to vascular prostheses, and more particularly relates to vascular grafts impregnated with a heparin-containing collagen sealant.

Vascular prostheses, commonly referred to as grafts, are typically used as soft tissue prostheses to replace damaged or diseased portions of blood vessels. During a surgical procedure, a damaged or diseased blood vessel portion may be removed and replaced with a vascular prosthesis. Complications, however, may occur as a result of the implanted prosthesis because of the body's natural tendency to reject foreign matter. More particularly, thrombosis or blood clotting within or upon the prosthesis may occur.

Precautions must be taken to minimize thrombosis and assure the patency of an implanted vascular prosthesis. Ideally, antithrombogenic properties should be imparted to the prosthesis. In addition to antithrombogenic properties, a vascular graft or prosthesis must be flexible and pliable to ensure that the prosthesis bends and flexes with the normal contours of the body into which it is transplanted. Without such flexibility, normal healing and acceptance by the body of the graft may not occur.

Vascular grafts or prostheses must also be porous to promote an ingrowth of tissue within or upon the vascular graft. More particularly, the exterior surface of the vascular prosthesis should include pores large enough to facilitate the entry of connective tissue and connective tissue cells such as fibroblasts, i.e., the ingrowth of the perigraft tissue. Generally, the larger the pore size, the better the ingrowth of the tissue into the wall from the perigraft tissue.

The interior surface should include pores that are not so large as to allow leakage of blood into surrounding tissues but large enough to promote tissue ingrowth. Blood leakage into surrounding tissues increases the likelihood of infection. The more porous the vascular graft substrate, the greater the tendency to hemorrhage during and after implantation.

Much effort has gone into hemostatic control, i.e., reducing the initial high rate of blood seepage into surrounding tissue from highly porous vascular graft substrates during and immediately after surgery. U.S. Pat. Nos. 3,805,301 and 4,047,242, assigned to the assignee of the subject application, disclose synthetic vascular grafts that are sufficiently porous to permit tissue ingrowth and allow firm attachment of a neointimal lining in the graft.

The vascular grafts disclosed within the U.S. Pat. Nos. 3,805,301 and 4,047,242 patents, however require a general procedure for implantation which includes the step of pre-clotting. During pre-clotting, the graft is immersed in the blood of the patient ex-vivo and allowed to stand for a period of time sufficient for clotting the porous substrate. Without the preclotting, excessive bleeding would occur when blood begins to flow into the vascular graft.

Emersion within a patients blood to pre-clot a graft, however, leaves the graft lumen highly thrombogenic due to the presence of a high concentration of thrombin on the intraluminal surface of the vascular graft. As the blood passes the thrombin buildup, the thrombin attracts platelets, forming a thrombus or blood clot that may detract from the graft's patency.

Other attempts to limit hemorrhaging from implanted grafts during and immediately after surgery include impregnating the vascular graft substrate with gelatinous material, such as that described in U.S. Pat. No. 4,747,848. The impregnated graft is then crosslinked by chemically modifying amino groups of the gelatinous molecules so that they will chemically bond to one another. The crosslinked, impregnated graft provides a sealed structure which prevents or controls bleeding. Subsequent to implantation, the gelatinous material is degraded by hydrolysis, slowly increasing the porosity over time and allowing tissue ingrowth to occur.

Collagen is also well known as an agent which is effectively used to impregnate the pores of synthetic grafts in an effort to limit bleeding upon implantation. Collagen is an insoluble fibrous protein that occurs naturally in vertebrates as the chief constituent of connective tissue fibrils. The patency of grafts impregnated with collagen is high. Collagen impregnated within grafts is gradually biodegraded by the body, uncovering pores present in the graft substrate structure to allow for tissue ingrowth and healing. Collagen coatings, however, are known to attract thrombin agents which form thrombosis or blood clots on surfaces treated with collagen. This can potentially lead to occlusion within transplanted grafts, the problem being especially acute in blood vessels having diameters of 10 mm or less.

U.S. Pat. No. 5,197,977, assigned to the assignee of the present invention, discloses a collagen-impregnated vascular graft which is effective in preventing blood leakage and which also does not require additional processing such as preclotting prior to use. The collagen-impregnation also slowly degrades in the body to enable host tissue ingrowth.

The collagen source with which the vascular graft is impregnated is a fibrous dispersion of high purity. The dispersion may also act as a reservoir for the sustained release of drug materials, such as anti-bacterial agents, anti-thrombogenetic agents and anti-viral agents, in an attempt to minimize bacterial infection and thrombosis subsequent to implantation.

Heparin is a chemical agent that prevents the clotting of blood, i.e., an anticoagulant. Conventional techniques for preparing collagen-heparin dispersions typically result in the precipitation of collagen from the collagen dispersion upon the addition of heparin in sufficient quantity to effectively prevent thrombosis upon grafts impregnated thereby. To prepare a graft with collagen using conventional methods therefore allows for only small quantities of heparin to be added to the sealant.

It is therefore an object of the present invention to provide a collagen-heparin dispersion which overcomes the aforementioned problems of the prior art, and method for forming the same.

It is another object of the present invention to provide a collagen-heparin dispersion in ratios of collagen to heparin such that thrombogenic events are minimized resulting from the implantation of a graft treated with the dispersion.

It is still another object of the present invention to provide a synthetic vascular graft which does not require pre-clotting with a patient's blood prior to implantation, and method for forming the same.

It is another object of the present invention to provide a collagen and heparin impregnated synthetic vascular graft that is coated with heparin to prevent thrombus formation and inhibit smooth muscle cell anastomotic hyperplasia after implantation, and method of forming the same.

It is yet another object of the present invention to provide a collagen and heparin impregnated synthetic vascular prosthesis which minimizes blood loss after implantation, and method for forming the same.

It is still another object of the present invention to provide a collagen and heparin impregnated synthetic vascular prosthesis that promotes cell ingrowth and enhances the rate and degree of healing within a patient's body after implantation, and method for forming the same.

It is still a further object of the present invention to provide a collagen and heparin impregnated vascular prosthesis that releases heparin at a sustained or controlled rate when implanted into a patient's body, and method for forming the same.

Still other objects and advantages of the invention will in part be obvious and will in part be apparent from the detailed description of the invention that follows.

SUMMARY OF THE INVENTION

The present invention includes a method of sealing a synthetic vascular prothesis to prevent thrombus formation. The method includes the steps of providing a stable collagen-heparin dispersion and applying the same to the synthetic vascular prosthesis to effectuate sealing and impart anti-thrombogenic properties thereto. Application of the stable collagen-heparin dispersion may be by coating or impregnating the prosthesis with the dispersion. The method particularly focuses on preparing a stable collagen-heparin dispersion at alkaline pH, preferably within a range of from about 9 to about 11, and, most preferably, at a pH of approximately 10. The collagen may be crosslinked by chemical or physical techniques subsequent to application to the synthetic vascular prosthesis.

The present invention also provides a synthetic vascular prostheses comprised of a flexible, porous, tubular substrate having an intraluminal and an extraluminal surface and fabricated from any conventional stitch structure, such as a knit, weave or braid. Double or single velours may also be employed. At, a minimum, the intraluminal surface is coated or impregnated with a stable collagen-heparin dispersion prepared with an alkaline dispersion of collagen and heparin, although all surfaces may be contacted with the dispersion. The ratio of collagen to heparin may be greater than or equal to one as a result of the alkaline collagen-heparin dispersion of this invention. The substrate may be a three-dimensional braid, a knit, a weave or a velour structure.

Also included is a collagen-heparin impregnated vascular prosthesis with a synthetic tubular substrate having an extraluminal and an intraluminal surface, prepared by the process of this invention. The process from which the vascular prosthesis is derived includes providing a stable alkaline dispersion of collagen and heparin and applying the dispersion to at least the intraluminal surface of the tubular substrate thereby providing an improved antithrombogenic seal to the vascular prosthesis.

The stable alkaline dispersion allows for more heparin and more collagen in solution, resulting in an improved ability to effectively coat and impregnate interstitial spaces within the textile material comprising the vascular prosthesis. The resulting vascular prothesis produced by the process of this invention, may minimize thrombus formation and smooth muscle cell hyperplasia on the intraluminal surface of the vascular prosthesis after implantation.

BRIEF DESCRIPTION OF THE DRAWINGS

FIG. 1 is a partial cut away side perspective view of a vascular graft made in accordance with present invention; and FIG. 2 is a partial cut away side perspective view of a branched vascular graft of the type illustrated in FIG. 1.

DETAILED DESCRIPTION OF THE PREFERRED EMBODIMENT

A vascular graft 20 constructed in accordance with the method of present invention is shown in FIG. 1. For purposes of describing he present invention, the terms "graft", "prosthesis" and "vascular graft" are interchangeably used in describing the methods apparatus and structures referred to herein. Vascular graft 20 includes a porous, tubular substrate portion 22 preferably formed of a synthetic material such as polyethylene terephthalate (commonly marketed under the trademark DACRON).

Generally, the porosity of the DACRON substrate ranges from about 2000 to 3000 ml/min-cm$^2$ (purified water at 120 mm Hg). Tubular substrate portion 22 is not limited, however, to DACRON. Tubular substrate portion 22 may be formed of any porous bio-compatible, filamentary synthetic material known to those skilled in the art which permits tissue ingrowth and is capable of maintaining an open, intraluminal passageway for the flow of blood after implantation.

Tubular substrate portion 22 may take on various forms. For example, tubular substrate portion 22 may be formed with an inner and outer velour surface such as the prostheses described in commonly owned U.S. Pat. Nos. 4,047,252 and 4,842,575.

For example, U.S. Pat. No. 4,047,452 discloses a double-velour synthetic vascular graft produced by a warp-knitting machine using a double needle bar. The trellis of the graft is made from a yarn with counts from 30 to 150 denier; preferably singly ply. Loops project from the trellis both on the inner and outer surfaces of the graft to provide for more effective ingrowth of tissue without impeding the flow of blood through the tubular body.

The knit fabric is compacted to decrease the size of pore openings and therefore the porosity of the fabric. Thereafter, the graft is clumped to impart uniform, regular, circular corrugations to provide uniform strength over the entire graft surface of the graft tubing and to minimize kinking and the propensity of the fabric to collapse.

U.S. Pat. No. 4,842,575 discloses a synthetic collagen-impregnated vascular graft which may be bifurcated. The grafts typically employ a DACRON warp knit fabric of varying diameter and porosity. The disclosures of U.S. Pat. Nos. 4,047,252 and 4,842,575 are incorporated herein by reference.

FIG. 1 shows an intraluminal surface 24 of tubular substrate portion 22 that is impregnated with and sealed by an application of the collagen-heparin dispersion of the present invention. The collagen-heparin coating imparts both hemostatic and anti-thrombogenic properties to a surface 26 of vascular graft 20. Bleeding is minimized, therefore, during and immediately after surgery. In addition, thrombin formation and accompanying stenosis are minimized within the vascular graft.

Collagen is a well known hemostatic agent used for coating porous, vascular synthetic grafts. Collagen applied thereby prevents blood seepage into surrounding tissue during and immediately after surgery. In addition to preventing blood loss, collagen is readily accepted by the body and may promote cell ingrowth and enhance the rate and degree of healing.

Methods for adhering collagen to a porous graft substrate typically include applying a collagen dispersion to the substrate, allowing it to dry and repeating the process. Collagen dispersions are typically made by blending insoluble collagen (approximately 1–2% by weight) in a dispersion at acidic pH (a pH in a range of 2 to 4).

The dispersion is typically injected via syringe into the lumen of a graft and massaged manually to cover the entire inner surface area with the collagen slurry. Excess collagen slurry is removed through one of the open ends of the graft. Coating and drying steps are repeated several times to provide sufficient treatment.

A collagen coated and/or impregnated prosthesis, however, tends to absorb or accept fibrinogen on its blood contacting surfaces, forming a fibrin matrix thereon. Growing fibrin strands within a fibrin matrix forms a thrombus or clot. Typically, an anticoagulant such as heparin is administered prior to the insertion of the graft to prevent clotting and consequential occlusion.

Collagen may also be utilized as a vehicle for the controlled release of pharmacological agents such as antibiotics and growth factors, as well as heparin. To accomplish this, the active (e.g., heparin) is provided in a collagen matrix which is coated on or impregnated within the graft. As the collagen biodegrades, the active is released and becomes bioavailable on the coated surface. Because of the conventional requirements for creating and performing a collagen-pharmaceutical coating, the amount of pharmaceuticals which can be dispersed within the coating has been limited.

Heparin has been used as an anti-coagulant for many years. Heparin is known to prevent thrombus build-up on an intraluminal surface to which it has been coated or bonded, such as intraluminal surface 24 of vascular graft 20.

After implantation of a vascular prosthesis with a collagen-heparin coating 26, heparin is released at a controlled rate thereby reducing the incidence of thrombosis or intraluminal surface 24. Collagen-heparin coating 26, by minimizing thrombosis and therefore stenosis within the prosthesis lumen enables production of vascular prosthesis with diameters that are smaller than diameters of previously available grafts, i.e., less than 10 mm (for implantation).

However, adding sufficient quantity of heparin to a conventional collagen dispersion (at the acidic pH) results in a collagen-heparin interaction which induces precipitation of the collagen from the dispersive phase. The result is that less collagen is available for application to the prosthetic substrate.

This interaction is believed to be the result of the negatively charged heparin molecule ionically interacting with the positively charged collagen molecules. However, this ionic interaction occurs regardless of whether the event proceeds above or below the isoelectric point of collagen.

The isoelectric point of limed, insoluble collagen, a pH of about 4, is that pH value at which the collagen molecules do not move in an electric field. Typically, precipitation of a colloid from suspension will occur above or below the colloid's isoelectric point; that is, with a change in pH in either the positive or negative direction.

The result of the ionic interaction is that water is forced from the collagen molecule causing a significant increase in the viscosity of the precipitate. This renders impregnation of the vascular prothesis extremely difficult. Vascular grafts coated or impregnated with a collagen-heparin dispersion prepared in a conventional manner must accordingly make due with a minimum of heparin to prevent the coagulation of the coating dispersion. That is, the conventional ratio of collagen to heparin was required to be many times greater than one in order to have sufficient collagen for sealing, yet, prostheses having such sealant compositions lacked sufficient heparin to be antithrombogenic.

The present invention overcomes the problems associated with the combination of collagen and antithrombogenic effective amount of heparin in dispersion. The present invention provides a unique method of preparing the collagen-heparin dispersion which avoids the precipitation of collagen that is typical of the prior art with the addition of substantial amounts of heparin.

The collagen dispersion of this invention is formed at an alkaline pH to provide a vehicle for adding proportionally large amount of heparin without inducing collagen precipitation. At conventional pH, either the ratio of collagen to heparin would need be extremely high to prevent viscosity increase, or the concentration of collagen and heparin needed to be extremely low, minimizing the effectiveness of collagen as a sealant. The biological properties of the heparin and collagen are not significantly altered at alkaline pH. Although a pH of about 10 is preferred, large amounts of heparin may be added to a collagen solution within a range of 9 to 11 without causing the collagen to precipitate out. The present invention preferably contemplates, however, dispersions with a ratio of heparin to collagen ranging between about 1:100 to 1:1.

The ratio of heparin to collagen by weight can be raised to 1 or greater if prepared according to the present invention without effecting the viscosity of the dispersion significantly, since the precipitation phenomenon and resultant loss of water does not occur. As a result, the interstitial spaces of a synthetic or textile type vascular prothesis are readily impregnated with the collagen-heparin dispersion with a significantly increased amount of heparin than those of the prior art.

Because of the increased heparin content in the collagen-heparin coating, a vascular prosthesis impregnated by the method of this invention such as that shown in vascular prosthesis 20, possesses enhanced antithrombogenic properties on its surface. Further, the improved healing response of the impregnated vascular prothesis inhibits smooth muscle anastomotic hyperplasia, i.e., an abnormal build up of smooth muscle cells at the surgical connection. Such results provide for a graft with a prolonged patency.

The following example is set forth to illustrate the method of preparing the collagen-heparin dispersion of the invention and applying it to a vascular graft. The examples are set forth for the purpose for illustration and are not intended in a limiting sense.

EXAMPLE 1

A 1.44% collagen slurry was prepared at a pH of 3.47 at 25° C. Four (4) drops/100 ml of 10M NaOh was added to raise the pH of the collagen slurry to 10.5. 50 grams of the collagen slurry was transferred to a 1000 ml volumetric flask. An amount of 0.72 g of heparin was added to the collagen slurry. No change in the state of the slurry occurred when this quantity of heparin was added to form a collagen-heparin dispersion.

The experiment was repeated varying the pH of the collagen prior to the addition of heparin, that is, the addition of 0.72 g of heparin to a 50 g portion of 1.44% collagen slurry. The pH was varied to find an operable range of solution in which a sufficient antithrombogenic amount of heparin may be added without inducing collagen precipitable.

When the pH was dropped to 10.0 by the addition of NaOh, there was no collagen precipitation upon the addition of 0.72 of heparin. When the pH was reduced to merely 6.4, there was a 50% precipitation. When the pH was further reduced to 4.50, there was a 90% percipitation.

The collagen-heparin dispersion i.e., 50 grams of 1.44% collagen slurry in which 0.72 g of heparin has been added was then applied to a bifurcated vascular graft 30 (FIG. 2) thereby impregnating and coating the graft.

FIG. 2 shows a bifurcated vascular graft 30 impregnated with a collagen-heparin coating 38 of the present invention. Bifurcated vascular graft 30 comprises a main porous, synthetic tubular substrate 32 including bifurcated portions 34 formed from a biologically compatible filamentary material. The graft may be constructed in any manner known to those skilled in the art for providing a porous vascular prosthesis which permits tissue ingrowth and maintains an open lumen for the flow of blood.

An inner surface 36 of porous, synthetic tubular substrate 32, including bifurcated portions 34, is impregnated with the collagen-heparin dispersion of the present invention. Collagen-heparin coating 38 is formed thereon. The impregnated vascular graft 30 showed a low incidence of bleeding as well as an increased absorbance of heparin. After implantation, the grafts are expected to display a lower incidence of thrombotic events occurring on either the coated surfaces 36 of tubular substrate portions 32 and bifurcated portions 34.

The specific embodiments of the vascular graft impregnated with a collagen-heparin sealant identified in this disclosure are not limited thereto and may be varied without materially effecting the anti-thrombogenic property of a vascular graft fabricated according to the invention. The invention accordingly is not limited to any precise embodiment disclosed and various other changes and modifications may be effected therein by one skill of the art without departing from the scope or spirit of the invention.

What is claimed is:

1. A method of sealing a synthetic vascular prosthesis with a collagen-heparin composition, comprising the steps of:

preparing a stable collagen-heparin dispersion at alkaline pH within a range from about 9 to about 11, wherein said dispersion is maintained within a pH range of from about 9 to about 11; and applying said dispersion to said prosthesis to effectuate sealing and impart enhanced antithrombogenic properties thereto.

2. A method as defined by claim 1, wherein said prosthesis is impregnated with said dispersion.

3. A method as defined by claim 1, wherein said prosthesis is coated with said dispersion.

4. A method as defined by claim 1, wherein the collagen-heparin dispersion is prepared at a pH of about 10.

5. A method as defined by claim 1, wherein the collagen-heparin dispersion has a ratio of heparin to collagen within a range of about 1:100 to about 1:1.

6. A synthetic vascular prosthesis as defined by claim 1, wherein the collagen applied to said prosthesis is crosslinked.

7. A collagen-heparin impregnated vascular prosthesis including a synthetic tubular substrate with an extraluminal and an intraluminal surface, prepared by a process comprising the steps of:

preparing a stable collagen-heparin dispersion at alkaline pH within a range from about 9 to about 11, wherein said dispersion is maintained within a pH range of from about 9 to about 11; and applying said dispersion to at least said intraluminal surface of said tubular substrate to provide an improved antithrombogenic seal to said prosthesis.

8. A synthetic collagen-heparin impregnated vascular prosthesis as defined by claim 7, wherein said process includes applying said dispersion to a three-dimensional braided structure.

9. A synthetic collagen-heparin impregnated vascular prosthesis as defined by claim 7, wherein said process includes applying said dispersion to a knitted substrate.

10. A synthetic collagen-heparin impregnated vascular prosthesis as defined by claim 7, wherein said process includes applying said dispersion to a woven substrate.

11. A synthetic collagen-heparin impregnated vascular prosthesis as defined by claim 7, wherein said process includes supplying said dispersion in a ratio of collagen to heparin of not less than one.

12. A synthetic collagen-heparin impregnated vascular prosthesis as defined by claim 7, wherein said process includes crosslinking said collagen after it is applied to said prosthesis.

13. A synthetic collagen-heparin impregnated vascular prosthesis as defined by claim 7, wherein said process includes providing said dispersion at pH of approximately 10.

14. A method of preparing a stable collagen-heparin dispersion that is useful for treating implantable synthetic prostheses, comprising the steps of:

mixing collagen and water to prepare a collagen dispersion in which the percentage of collagen is 2% by weight;

adding sodium hydroxide in sufficient amounts to said dispersion to raise the pH to an alkaline pH level within a pH range of about 9 to 11 to avoid collagen precipitation; and adding heparin to said dispersion in an amount in a ratio of heparin to collagen of from about 1:100 to about 1.1.

* * * * *